US011147932B2

(12) United States Patent
    Alexandersson

(10) Patent No.: US 11,147,932 B2
(45) Date of Patent: Oct. 19, 2021

(54) MEDICAMENT DELIVERY DEVICE HAVING A CAP ASSEMBLY

(71) Applicant: SHL MEDICAL AG, Zug (CH)

(72) Inventor: Oscar Alexandersson, Haninge (SE)

(73) Assignee: SHL MEDICAL AG, Zug (CH)

( * ) Notice: Subject to any disclaimer, the term of this patent is extended or adjusted under 35 U.S.C. 154(b) by 247 days.

(21) Appl. No.: 16/461,115

(22) PCT Filed: Oct. 30, 2017

(86) PCT No.: PCT/EP2017/077823
    § 371 (c)(1),
    (2) Date: May 15, 2019

(87) PCT Pub. No.: WO2018/091262
    PCT Pub. Date: May 24, 2018

(65) Prior Publication Data
    US 2020/0061309 A1    Feb. 27, 2020

(30) Foreign Application Priority Data
    Nov. 15, 2016  (EP) ..................... 16198888

(51) Int. Cl.
    *A61M 5/50*    (2006.01)
    *A61M 5/32*    (2006.01)
(52) U.S. Cl.
    CPC ........ *A61M 5/5086* (2013.01); *A61M 5/3204* (2013.01); *A61M 2005/3247* (2013.01)
(58) Field of Classification Search
    CPC .................... A61M 5/5086; A61M 5/3204
    See application file for complete search history.

(56) References Cited

U.S. PATENT DOCUMENTS

2015/0174325 A1*  6/2015  Young ................ A61M 5/2033
                                                        604/135
2016/0325044 A1  11/2016  Tschirren et al.
2018/0353705 A1  12/2018  Andre et al.

FOREIGN PATENT DOCUMENTS

CA        2803442 A1    1/2012
CN      103957969 A     7/2014
            (Continued)

OTHER PUBLICATIONS

Search Report issued in Taiwanese Patent Application No. 106138404 dated Mar. 19, 2019.

*Primary Examiner* — Emily L Schmidt
(74) *Attorney, Agent, or Firm* — McDonnell Boehnen Hulbert & Berghoff LLP

(57) ABSTRACT

The present disclosure relates to a medicament delivery device comprises: a housing having a proximal end and a distal end; a medicament container positioned in the housing and having a medicament delivery member shield; a medicament delivery mechanism associated with the medicament container; an activation member operably connected to the medicament delivery mechanism and longitudinally movable in relation to the housing from an extended position to a retracted position to activate the medicament delivery mechanism; and a removable cap assembly comprising a deshielder, an inner tubular integrity lock member having a resilient structure configured to interact with both a first engaging structure of the activation member and a second engaging structure of the housing for preventing the activation member from moving into the retracted position; and wherein the removable cap assembly further comprises an outer tubular cap body which is movable in relation to the housing and to the inner tubular integrity lock member from an initial position in which the outer tubular cap body is releasably connected to the housing and is disengaged from (Continued)

the inner tubular integrity lock member, to an intermediate position in which the outer tubular cap body is partially disengaged from the housing for giving tamper proof indication and in which the outer tubular cap body is fixedly engaged to the inner tubular integrity lock member for allowing the removal of the medicament delivery member shield.

15 Claims, 15 Drawing Sheets

(56) References Cited

FOREIGN PATENT DOCUMENTS

| | | | |
|---|---|---|---|
| CN | 105828851 | A | 8/2016 |
| EP | 2745866 | A1 | 6/2014 |
| TW | 201722489 | A | 7/2017 |
| TW | 201722493 | A | 7/2017 |
| WO | 2013006119 | A1 | 1/2013 |
| WO | 2014009705 | A1 | 1/2014 |
| WO | 2014/056635 | A1 | 4/2014 |
| WO | 2014131858 | A1 | 9/2014 |
| WO | 2016055334 | A1 | 4/2016 |
| WO | 2017084883 | A1 | 5/2017 |

\* cited by examiner

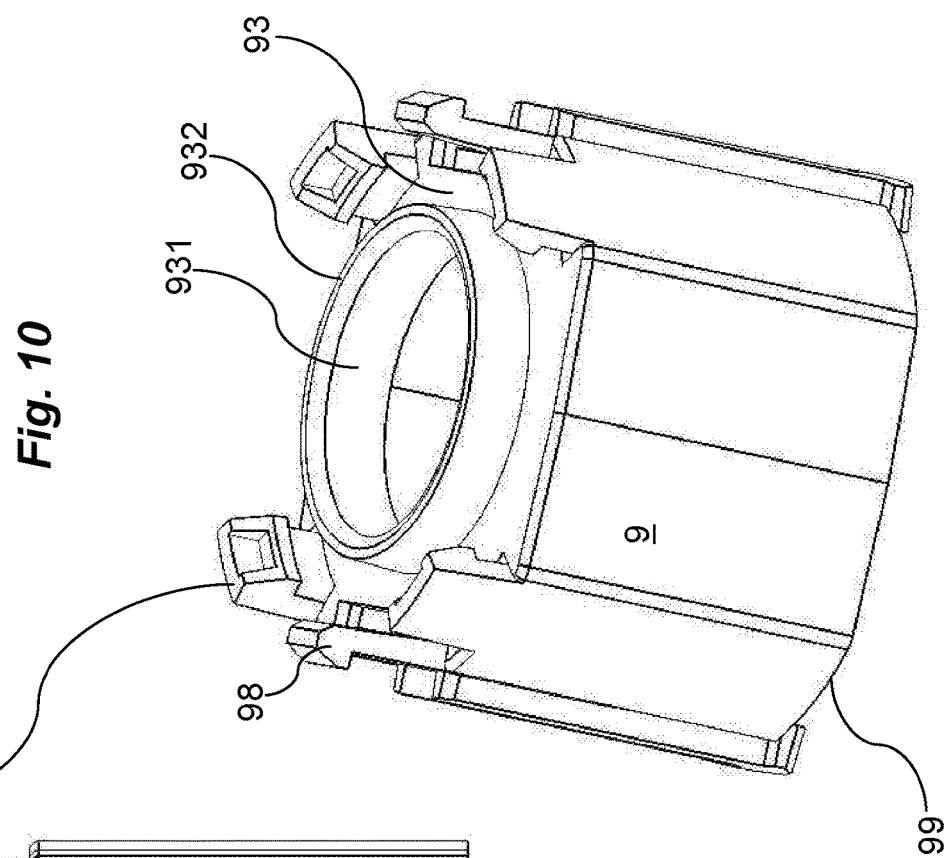
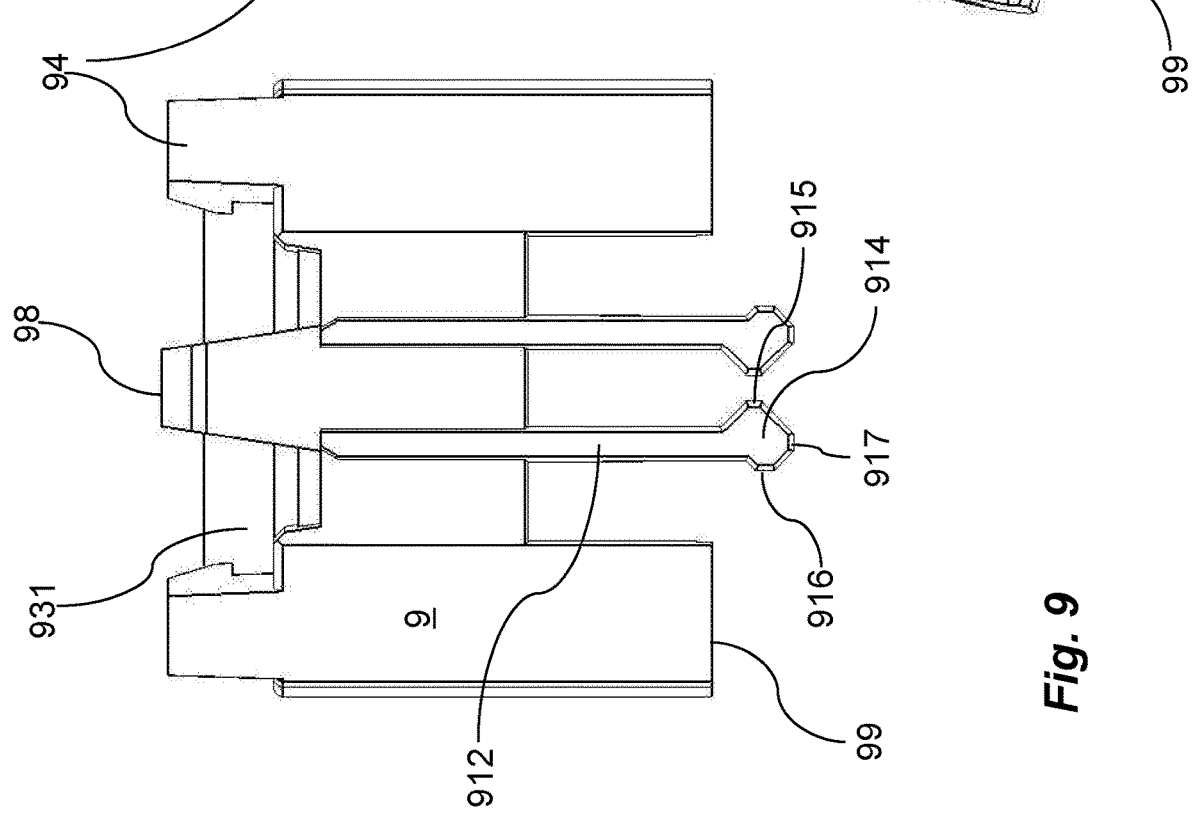
Fig. 10
Fig. 9

MEDICAMENT DELIVERY DEVICE HAVING A CAP ASSEMBLY

CROSS REFERENCE TO RELATED APPLICATIONS

The present application is a U.S. National Phase Application pursuant to 35 U.S.C. § 371 of International Application No. PCT/EP2017/077823 filed Oct. 30, 2017, which claims priority to European Patent Application No. 16198888.6 filed Nov. 15, 2016. The entire disclosure contents of these applications are hereby incorporated by reference into the present application.

TECHNICAL FIELD

The present disclosure generally relates to medicament delivery devices. In particular, it relates to a medicament delivery device having a removable cap assembly that prevents the medicament delivery device to be accidentally activated and that prevents a recapping.

BACKGROUND

Medicament delivery devices, such as injectors, auto-injectors and inhalers, typically comprise a housing in which a medicament container containing a medicament is to be arranged. Upon activation of the medicament delivery device, the medicament is expelled through a medicament delivery member, as for example a needle or a nozzle.

In injection devices where the medicament delivery member is a needle, said needle is protected and kept sterile. Thus, the medicament delivery member may be provided with a delivery member shield, or sheath, such as a Flexible Needle Shield (FNS) or a Rigid Needle Shield (RNS). The delivery member shield may thus be attached to the medicament container to cover the medicament delivery member.

More specifically, auto-injectors normally comprise an actuation mechanism for exerting a force to expel the medicament from the medicament container through the medicament delivery member, an activation member which may be a medicament delivery member cover coupled to the actuation mechanism for releasing the actuation mechanism to expel the medicament, and a cap connected to the front end of the housing for removing the delivery member shield. Some auto-injectors, as disclosed in WO2014131858 A1, also comprise a mechanical interlock which prevents actuation of the activation member prior to removal of the cap such that when the cap is removed, the mechanical interlock allows the actuation of the activation member.

Further, EP2745866A1 discloses also an auto-injector which comprises a housing for accommodating a medicament container with a needle, a force mechanism for applying a force to eject a liquid medicine from the medicament container, a biased needle cover sleeve having a flexible arm and wherein the cover sleeve is coupled to the force mechanism for releasing the force mechanism to cause an injection, a needle shield covering the needle, a cap connected to the front end of the housing for removing the needle shield. When the cap is attached to the housing, the needle cover sleeve is partially moved into the housing such that the flexible arm is deflected by a surface of the cap and kept in the deflected state by a surface of the housing such that actuation of the needle cover sleeve is prevented prior to removal of the cap. When the cap is removed, the needle cover is partially moved out from the housing such that flexible arm does not interact with the housing and allows the actuation of the needle cover sleeve.

SUMMARY

In view of the known prior art, it is noticed that a removable cap assembly has the function of providing mechanical protection to the medicament delivery member while attached to the housing and to remove the delivery member shield when at least part of the cap assembly is removed from the housing. However, there is a tangible risk that, the activation mechanism of the medicament delivery device may be influenced by any accidental or deliberate movement on the activation member during transportation or by accidentally dropping the medicament delivery device among others.

Thus, a general aim of the present disclosure is to provide a medicament delivery device having a simple and robust cap assembly having a common feature in the form of an integrity lock which prevents the medicament delivery device from being accidentally activated and that also prevents a recapping which gives an indication to the user that the device has been used or that the sterility of the medicament delivery member has been exposed.

This aim is achieved with a medicament delivery device having the features of the independent patent claim. Preferable embodiments of the invention form the subject of the dependent patent claims.

According to a main aspect, a medicament delivery device comprises: a housing having a proximal end and a distal end; a medicament container positioned in the housing and having a medicament delivery member shield; a medicament delivery mechanism associated with the medicament container; an activation member operably connected to the medicament delivery mechanism and longitudinally movable in relation to the housing from an extended position to a retracted position to activate the medicament delivery mechanism; and a removable cap assembly comprising a deshielder, an inner tubular integrity lock member having a resilient structure configured to interact with both a first engaging structure of the activation member and a second engaging structure of the housing for preventing the activation member from moving into the retracted position; and wherein the removable cap assembly further comprises an outer tubular cap body which is movable in relation to the housing and to the inner tubular integrity lock member from an initial position in which the outer tubular cap body is releasibly connected to the housing and is disengaged from the inner tubular integrity lock member, to an intermediate position in which the outer tubular cap body is partially disengaged from the housing for giving tamper proof indication and in which the outer tubular cap body is fixedly engaged to the inner tubular integrity lock member for allowing the removal of the medicament delivery member shield.

The removable cap assembly further comprises a cap closer which is fixedly connected to the inner tubular integrity lock member or integrally.

According to another aspect, the deshielder is fixedly attached between the integrity lock member and the cap closer.

Further, the outer tubular cap body comprises first connecting elements and the cap closer comprises second connecting elements arranged such that when the outer tubular cap body is in the initial position the first and second connecting elements are disengaged and when the outer tubular cap body is in the intermediate position the first and second connecting elements are engaged.

Moreover, the outer tubular cap body further comprises a third connecting element and the inner tubular integrity lock member a fourth connecting element configured to interact together when the outer tubular cap body is in the intermediate position such that the outer tubular cap body is fixedly engaged to the inner tubular integrity lock member.

According to another aspect, in the initial or in the intermediate position of the outer tubular cap body, the resilient structure of the inner tubular integrity lock member is configured to interact with both the first and the second engaging structures for preventing the activation member from moving into the retracted position.

According to a further aspect, the first engaging structure of the activation member comprises a guiding recess and a guiding protrusion. The guiding recess is substantially U-shaped and it is defined by two parallel longitudinally extending side walls, a transversal side wall and a bottom wall and wherein the guiding protrusion is arranged on the outer surface of the bottom wall of the guiding recess.

According to yet another aspect the resilient structure of the inner tubular integrity lock member comprises a pair of spaced apart longitudinally extending arms which are flexible in the transversal direction and which form a U-shaped cut-out portion between them. Each longitudinally extending arm has a distal free end having a first transversal inwardly extending lip, a second transversal outwardly extending lip and a distal top edge. Further, the first transversal inwardly extending lip has a shape configured to interact with a corresponding shape of the guiding protrusion for allowing the longitudinally extending arm to flex.

According to a further aspect, in the initial or in the intermediate position of the outer tubular cap body, the pair of spaced apart longitudinally extending arms are configured to extend longitudinally along the bottom wall of the U-shaped guiding recess and to receive the guiding protrusion in U-shaped cut-out portion defined by the pair of spaced apart longitudinally extending arms.

According to another aspect, the second engaging structure is formed as a U shaped slot or cut-out defined by a transversal edge and two spaced apart and opposite side edges and wherein each side edge form a transversal inwardly protrusion which presents an edge which forms part of a proximal rim of the housing. Each second transversal outwardly extending lip is releasably connected to a corresponding side edge of the U-shaped slot or cut-out of the housing for preventing the longitudinally extending arms to flex transversally outwards and thereby prevent the activation member from moving into the retracted position when the outer tubular cap body is in the initial or in the intermediate position.

Further, the medicament delivery device is an autoinjector.

BRIEF DESCRIPTION OF THE DRAWINGS

The specific embodiments of the inventive concept will now be described, by way of example, with reference to the accompanying drawings, in which:

FIGS. 9 and 10 illustrate additionally two further views of the inner tubular integrity lock member of FIGS. 7 and 8.

DETAILED DESCRIPTION

There will now be described with reference to FIGS. 1 to 21 of the accompanying drawings, according to the device of the present invention.

In the present application, when the term "distal part/end" is used, this refers to the part/end of delivery device, or the parts/ends of the members thereof, which is/are located the furthest away from the medicament delivery site of the patient. Correspondingly, when the term "proximal part/end" is used, this refers to the part/end of delivery device, or the parts/ends of the members thereof, which is/are located closest from the medicament delivery site of the patient.

Figure 1:
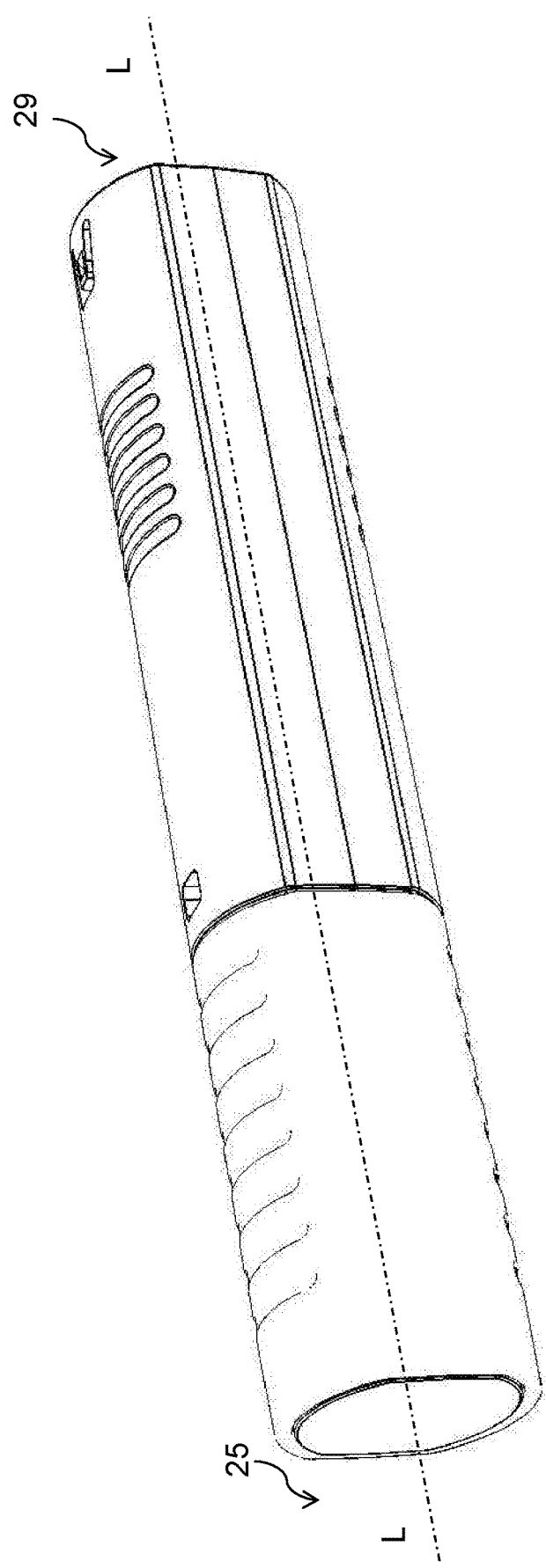
FIG. 1 illustrates a perspective view along the longitudinal L-axis of the medicament delivery device of the invention.
Figure 2:
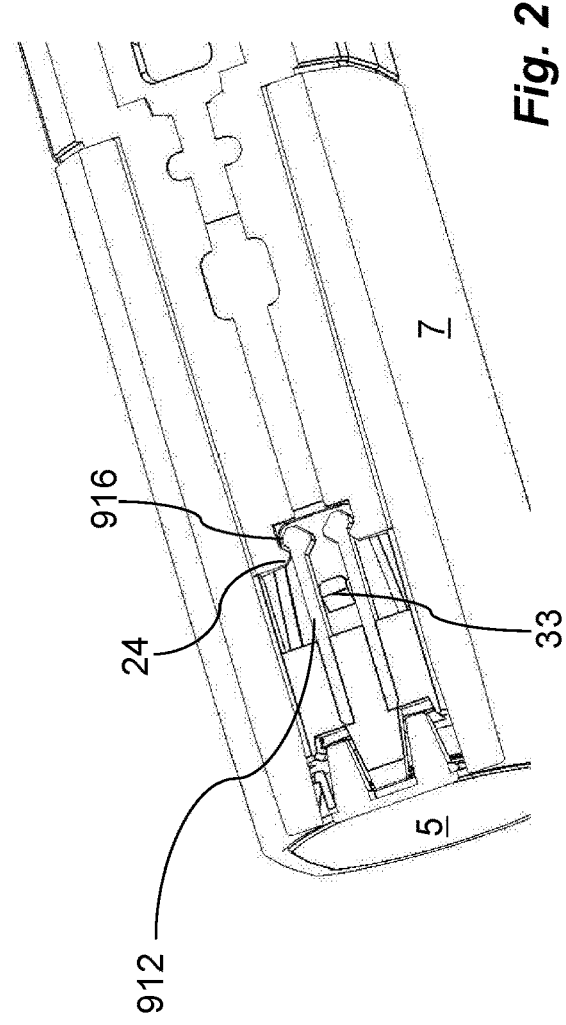
FIG. 2 illustrates a resilient structure through a transparent view of the outer tubular cap body in the initial position.

In FIGS. 1 and 2 it is shown a medicament delivery device 1 according to the present invention. The medicament delivery device 1 having a proximal end 25 and a distal end 29.

Figure 3:
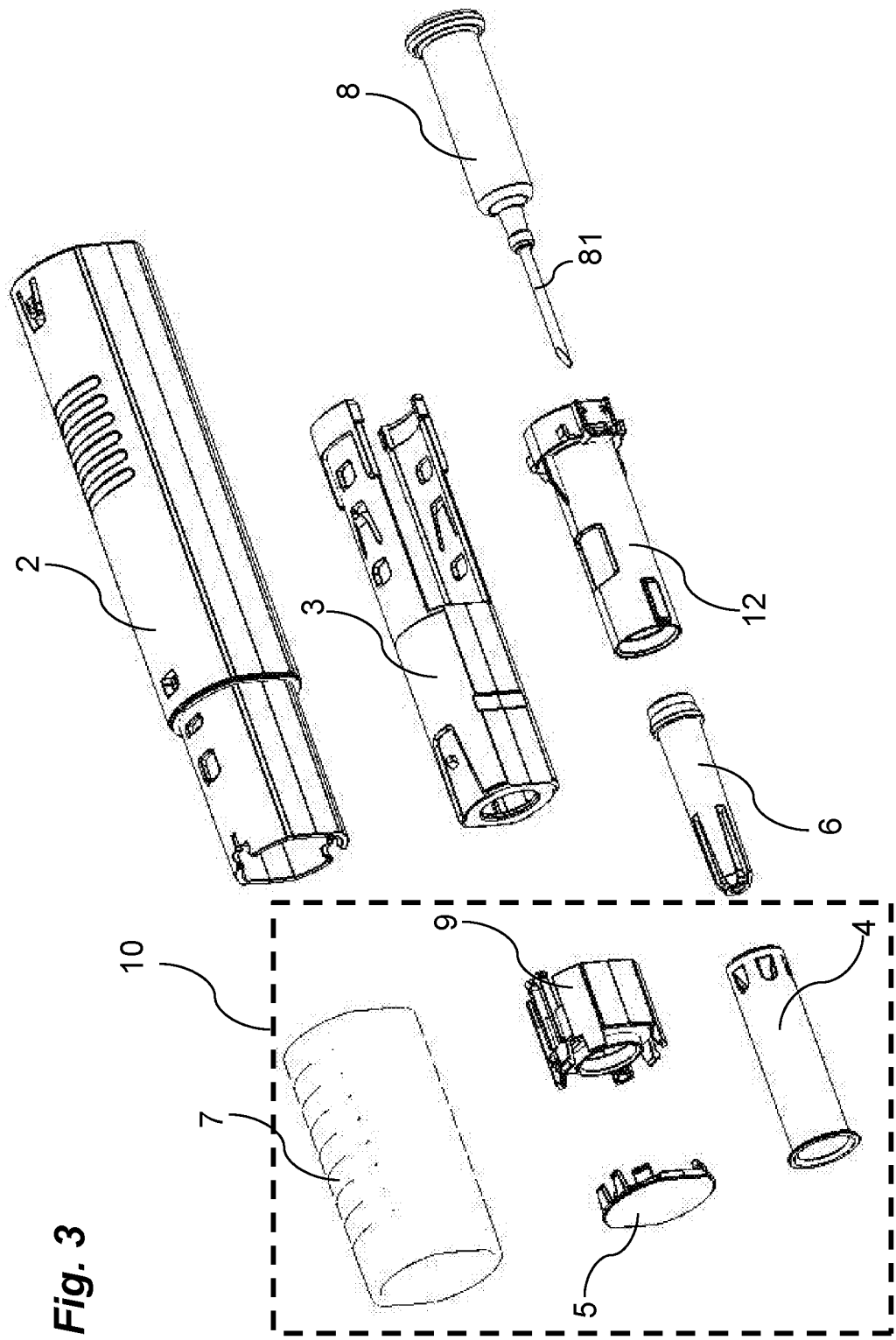
FIG. 3 shows an exploded perspective view of the medicament delivery device as disclosed by FIGS. 1 and 2.

FIG. 3 illustrates an exploded perspective view of the medicament delivery device of the invention according to FIGS. 1 and 2. The medicament delivery device 1 (not shown in FIG. 3) comprises a housing 2, a medicament container 8 having a medicament delivery member 81 herein depicted as a needle which is protected against external mechanical or biological damage by a medicament delivery member shield 6, a medicament container holder 12 configured to receive the medicament container 8, a medicament delivery mechanism (not shown) associated with the medicament container 8, an activation member 3 operably connected to the medicament delivery mechanism and longitudinally movable in relation to the housing 2 from an extended position to a retracted position to activate the medicament delivery mechanism, and a removable cap assembly to comprising a deshielder 4, an inner tubular integrity lock member 9, a cap closer 5, and an outer tubular cap body 7; wherein the outer tubular cap body 7 is movable in relation to the housing 2 and to the inner tubular integrity lock member 9 from an initial position in which the outer tubular cap body 7 is releasibly connected to the housing 2 and is disengaged from the inner tubular integrity lock member 9, to an intermediate position in which the outer tubular cap body 7 is partially disengaged from the housing 2 for giving tamper proof indication and in which the outer tubular cap body 7 is fixedly engaged to the inner tubular integrity lock member 9 for allowing the removal of the medicament delivery member shield 6. In the same spirit of the invention, there may be possible to manufacture two or more parts in one single unit, depending of the assembly requirements.

Figure 4:
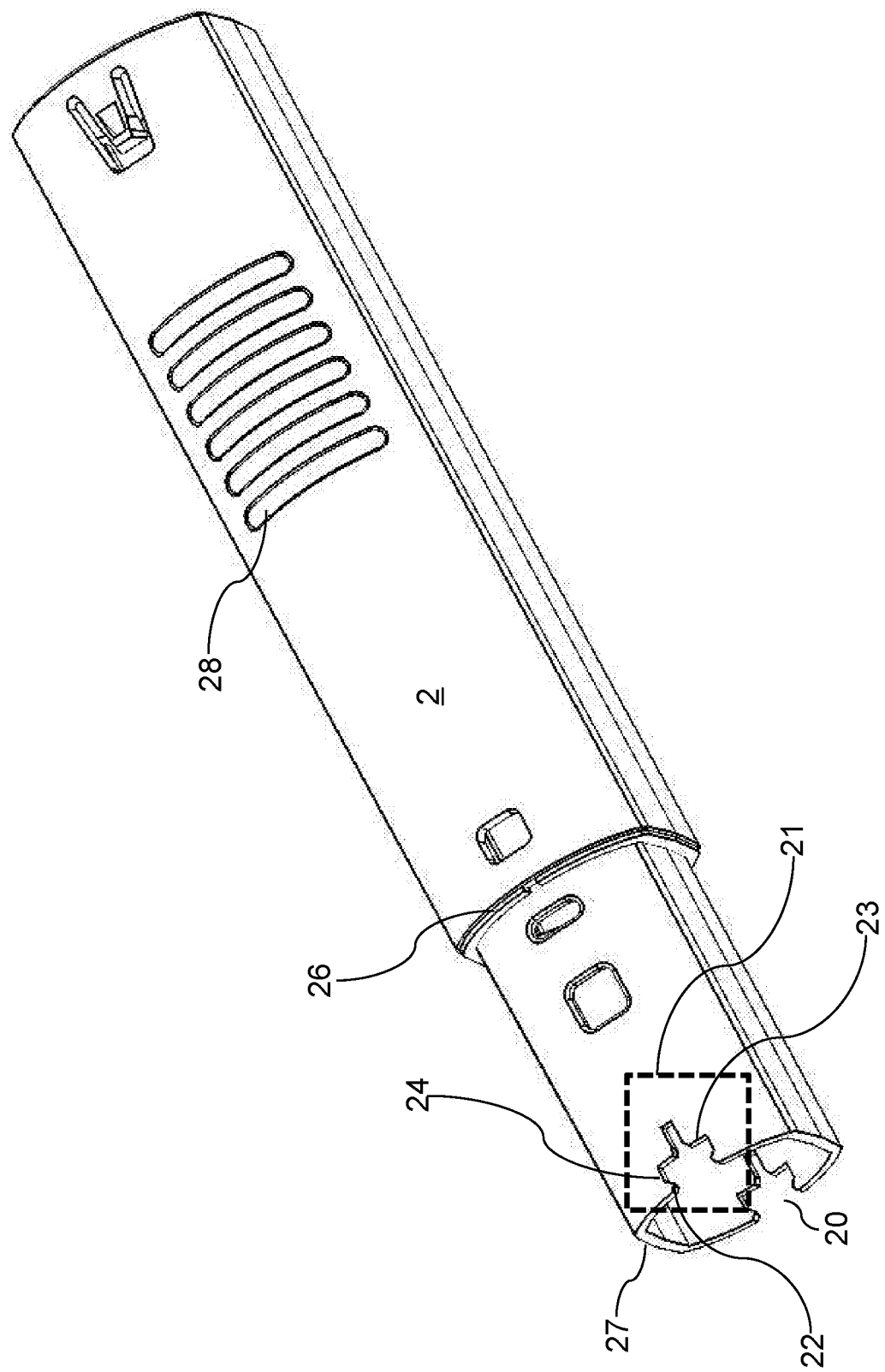
FIG. 4 shows a perspective view of a tubular housing as shown in FIG. 3.

FIG. 4 shows in more detail a perspective side view of the tubular housing 2 having a proximal and a distal portion and wherein the distal portion has a larger diameter than that of the proximal portion.

Figure 5:
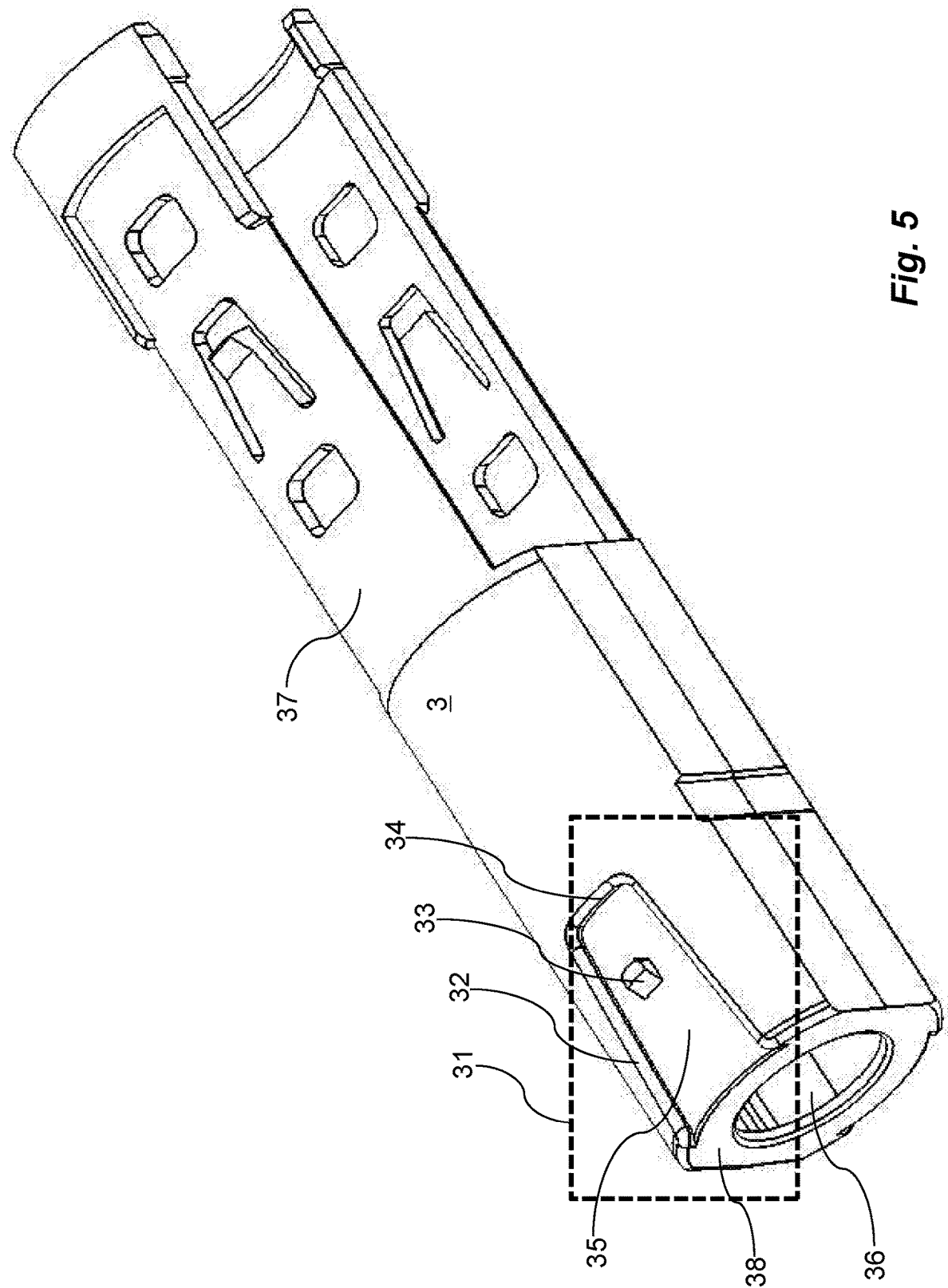
FIG. 5 shows a perspective view of an activation member as disclosed in the exploded view of FIG. 3.

A transversal wall 26 is formed by the transition from the distal portion and the proximal portion. The proximal portion of the housing 2 comprises a proximal rim 27 and a second engaging structure 21; and the distal portion comprises optional gripping elements 28. The proximal portion of the housing 2 is configured to partially and releasably receive the outer tubular cap body 7 as shown in FIG. 1. As seen in FIG. 4 two opposed second engaging structures 21 are depicted. Each second engaging structure 21 is formed as a slot or cut-out 20 defined by transversal edges 23 and two spaced apart and opposite side edges 24. Each side edge 24 forms a transversal inwardly protrusion which presents an edge 22 and wherein said edge 22 forms part of the proximal rim 27. FIG. 5 shows a more detailed view of the activation member 3, which is operably connected to a medicament delivery mechanism (not shown) at its distal part. The activation member 3 comprises two main segments: a proximal portion having two opposed first engaging structures 31 and a distal portion having two spaced apart longitudinal extending opposed tongues 37. Said opposite tongues 37 are configured to interact with the medicament delivery mechanism (not shown) of the medicament delivery device 1. The first engaging structure 31 according to FIG. 5 comprises a guiding recess and a guiding protrusion 33.

The guiding recess is substantially U-shaped and it is defined by two separated longitudinally extending side walls 32, a transversal side wall 34 and a bottom wall 35. The guiding protrusion 33 is arranged on the outer surface of the bottom wall 35. Furthermore, the activation member 3 comprises a transversal wall 38 having an opening channel 36.

Figure 6:
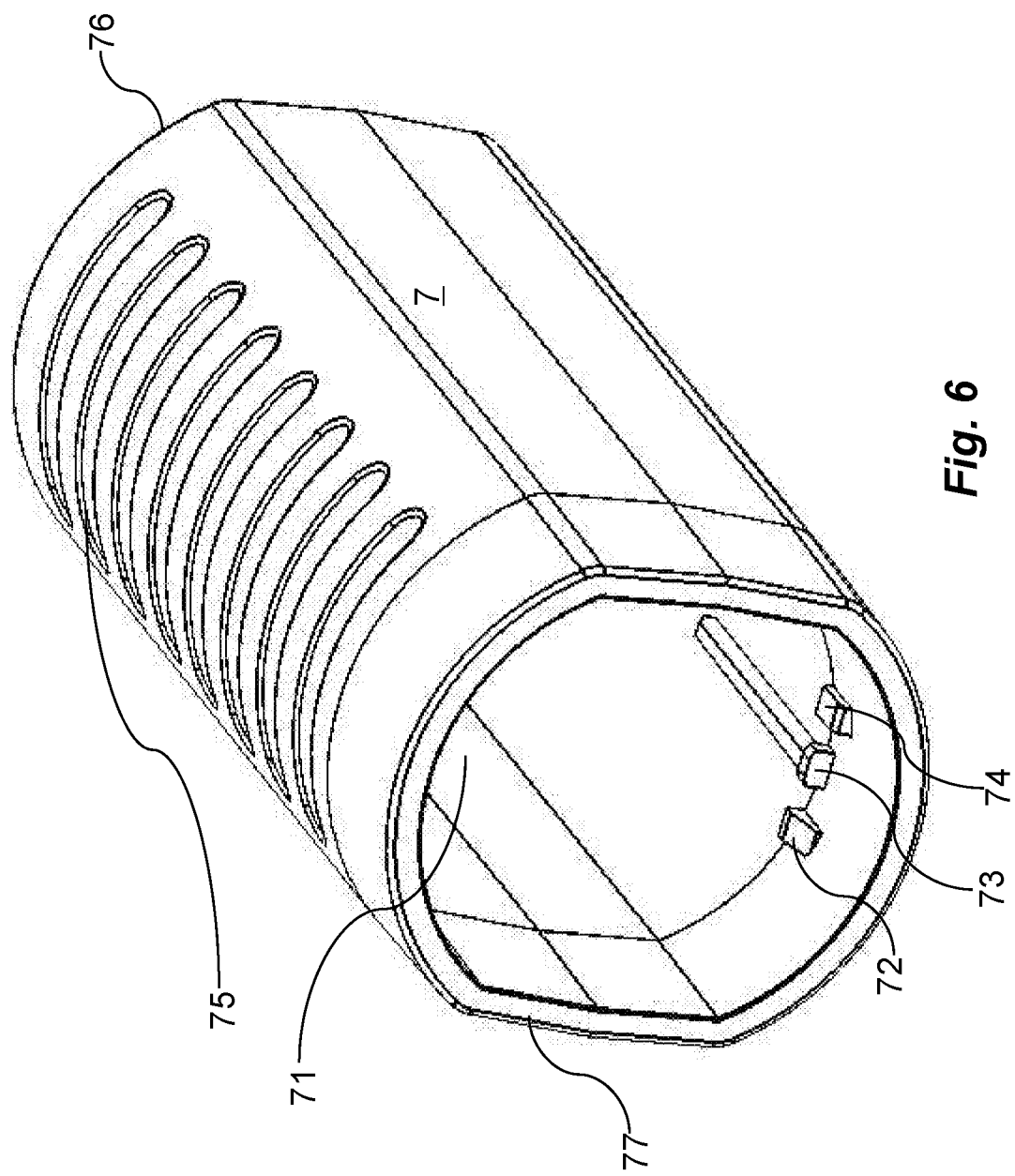
FIG. 6 illustrates a perspective view of the outer tubular cap body, wherein the grip elements and other parts are shown.

FIG. 6 illustrates in detailed a perspective view of the outer tubular cap body 7, which is removably connected to the tubular housing 2 along the L-axis as previously shown in FIG. 1. Further, the outer tubular cap body 7 comprises optional gripping elements 75 on its outer surface (also visible in FIG. 1) for facilitating an enhanced grip by the fingers/hands of a user on the outer tubular cap body 7, and an opening channel 71. The outer tubular cap body 7 further comprises at its distal end a distal rim 76 which is configured to dock/abut with the transversal wall 26 of the housing 2, and a proximal rim 77 at its proximal end. Moreover, the outer tubular cap body 7 comprises first connecting elements 72, 74 and a third connecting element 73 as explained below.

In the present embodiment, close to the proximal end and on the inner surface of the outer tubular cap body 7, the first and the third connecting elements 72, 73, 74 are two opposed sets of three radial inwardly directed protrusions. The first connecting elements are a radial inwardly directed protrusion 72 and a second radial inwardly directed protrusion 74 which are wedge shaped. The first radial inwardly directed protrusion 72 presents a longitudinally extending inclined elevation and a transversal stop wall facing towards the distal end. The second radial inwardly directed protrusion 74 presents a circumferentially extending inclined elevation and a transversal stop wall which is rotated 90 degrees clockwise in relation to transversal stop wall of the first radial inwardly directed protrusion 72. Between the first radial inwardly directed protrusion 72 and the second radial inwardly directed protrusion 74 is the third connecting element 73 which is a third radial inwardly directed protrusion 73. The third radial inwardly directed protrusion 73 is a "T" shaped rib presenting a long longitudinal extending rib and a short circumferential extending rib.

Figure 7:
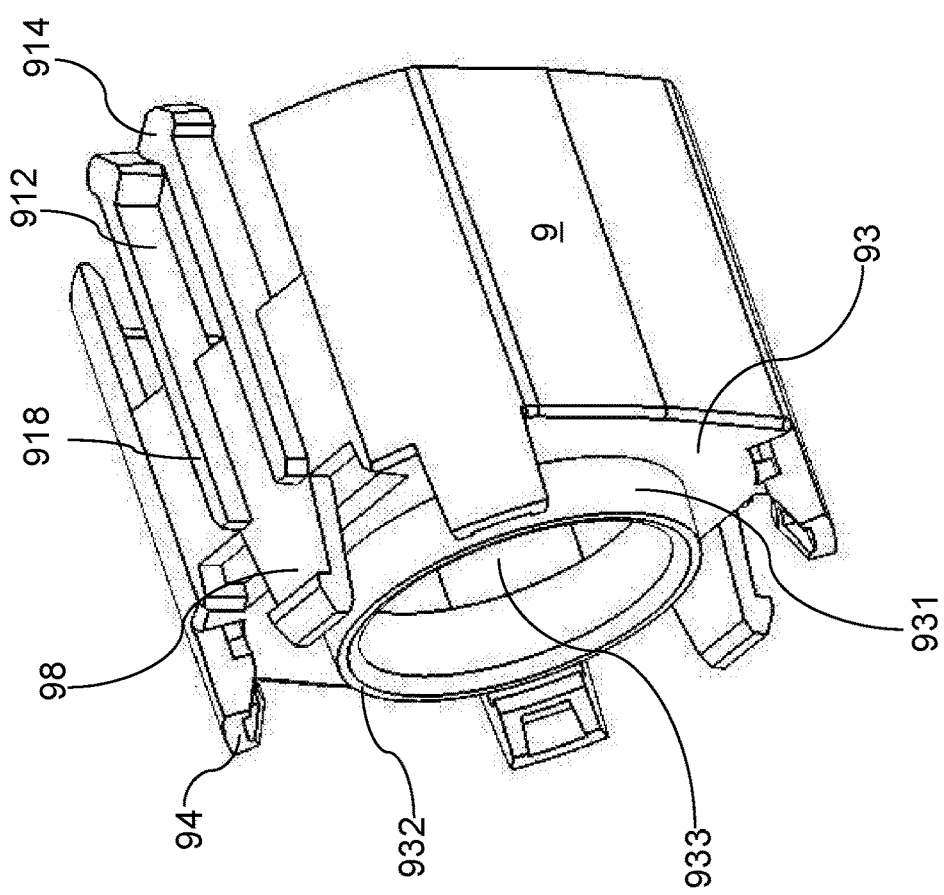

The inner tubular integrity lock member 9 is depicted in more detail in figures FIGS. 7-8 and FIGS. 9-10, since it is an essential part of the medicament delivery device 1. Focusing on the proximal portion of the inner tubular integrity member 9, FIG. 7 and FIG. 10 illustrate a proximal transversal wall 93 having a ring-shaped sleeve 931 with a sleeve rim 932 and an opening channel 933.

Figure 8:
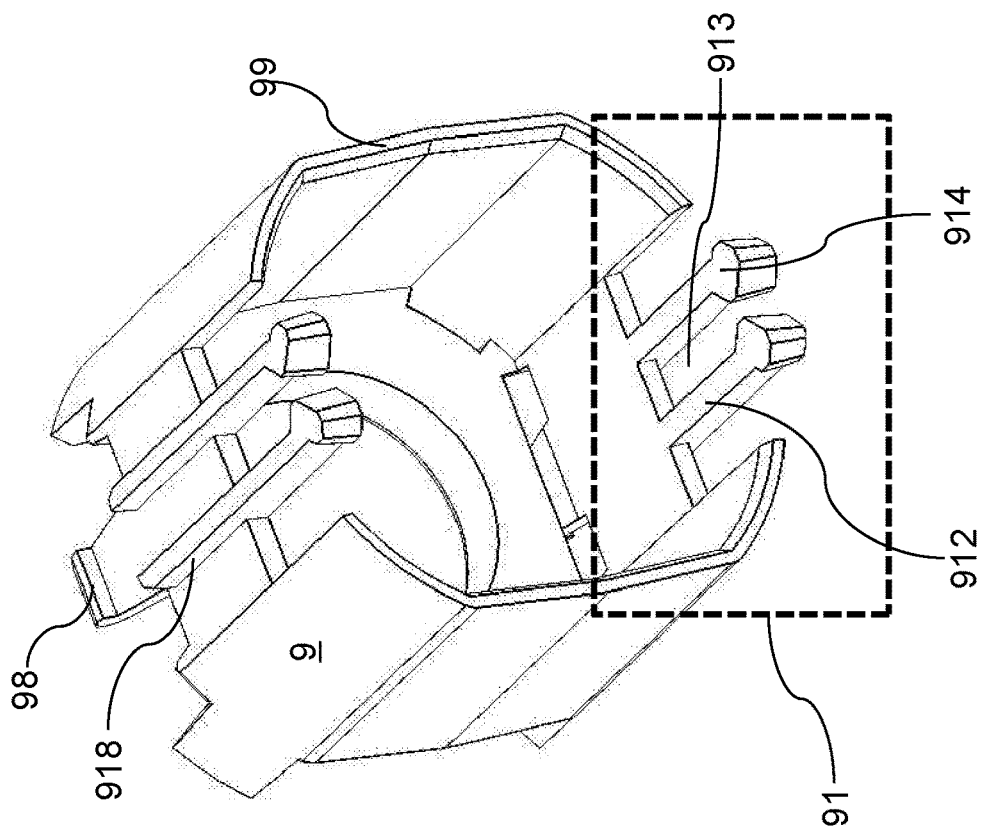
FIGS. 7 and 8 show two different perspective views of an inner tubular integrity lock member as disclosed in the exploded view of FIG. 3 in different angles.

The tubular integrity member 9 comprises on its outer surface four equally spaced apart resilient longitudinal proximally extending legs 94 and a fourth connecting element 98 which are two resilient opposite spaced apart longitudinal proximally extending flaps 98. Each resilient longitudinal proximally extending leg 94 and each resilient opposite spaced apart longitudinal proximally extending flap 98 has at its proximal end a wedge shaped engagement element. The wedge shaped engagement elements of the resilient longitudinal proximally extending legs 94 extend radially inwards and the wedge shaped engagement elements of the resilient opposite spaced apart longitudinal proximally extending flaps 98 extend radially outwards. Further, the tubular integrity member 9 comprises on its outer surface a resilient structure 91. As seen in FIG. 8 two opposed resilient structures 91 are depicted. Each resilient structure 91 is defined by a pair of flexible spaced apart longitudinally extending arms 912 which extend longitudinally towards the distal end i.e. opposite to the direction of the resilient opposite spaced apart longitudinal proximally extending flaps 98.

FIGS. 7-8 show in perspective views, the inner tubular integrity lock member 9 comprising a distal rim 99 and the pair of spaced apart longitudinally extending arms 912 which form a U-shaped cut-out portion 913 between them. The pair of spaced apart longitudinally extending arms 912 extends a certain distance from the distal rim 99 of the inner tubular integrity lock member 9 and also towards the proximal end defining radially outward extending ribs 918.

As seen in FIG. 9 each longitudinally extending arm 912 has a distal free end 914 provided with a first transversal inwardly extending lip 915, a second transversal outwardly extending lip 916 and a distal top edge 917.

Each second transversal outwardly extending lip 916 has a shape configured to interact with a corresponding shape formed in each side edge 24 of the U-shaped slot or cut-out 20 of the housing 2 for allowing a distal portion of each longitudinally extending arm 912 to flex transversally inward and each first transversal inwardly extending lip 915 has a shape configured to interact with a corresponding shape of the guiding protrusion 33 arranged on the bottom wall 35 of the guiding recess of the activation member 3 for allowing the longitudinally extending arm 912 to flex transversally outward when the inner tubular integrity lock member 9 is proximally displaced a certain distance in relation to the housing 2 and to the activation member 3.

Figure 12:
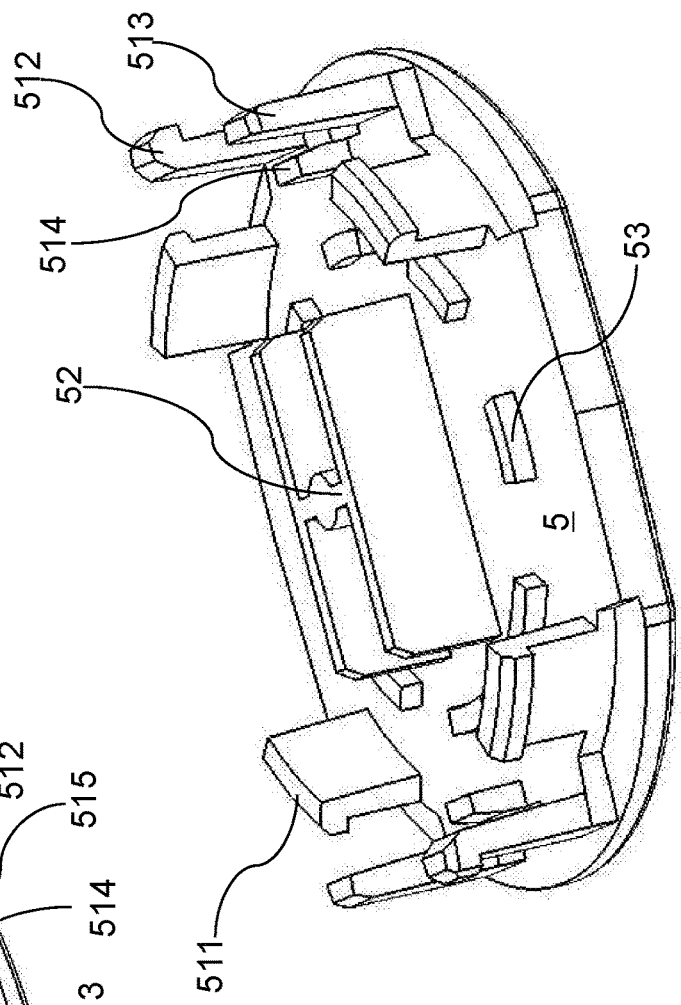
FIGS. 11 and 12 show two perspective views of a cap closer as disclosed in the exploded view of FIG. 3 in different angles.
Figure 11:
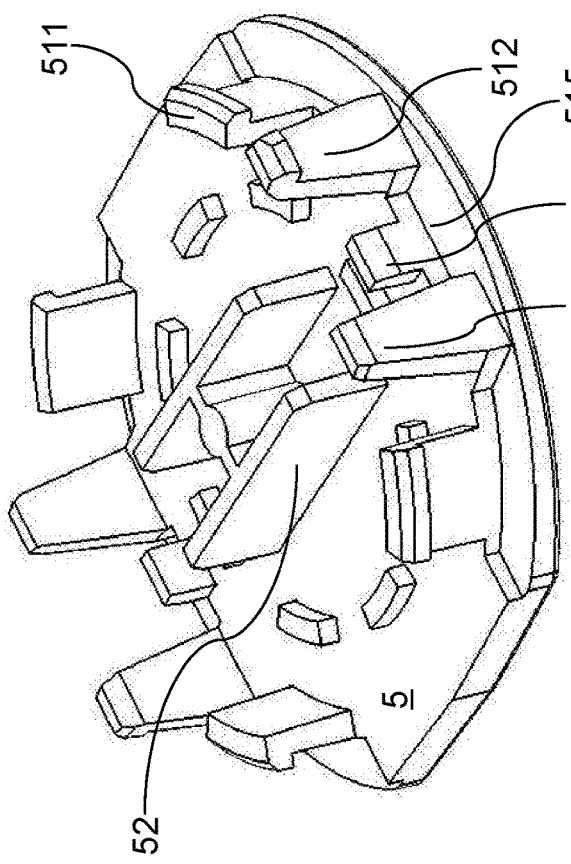

FIGS. 11-12 illustrate two different perspective views of the distal face of the cap closer 5. The cap closer 5 comprises a "H" leg elevation 52, spaced apart inner circular ledges 53, four equally separated distal extending flaps 511 having wedge shaped engagement elements which extend radially outwards, second connecting elements 512, 513 which in the present embodiment are two distal extending tongues 512 having wedge shaped engagement elements which extend radially outwards and two distal extending ledges 513 without any engagement elements, two receiving parts 515 wherein each receiving part 515 is located between one distal extending tongue 512 and one distal extending ledge 513, and two distal extending protrusions 514 wherein each distal extending protrusion 514 is also located between one distal extending tongue 512 and one distal extending ledge 513.

Figure 13:
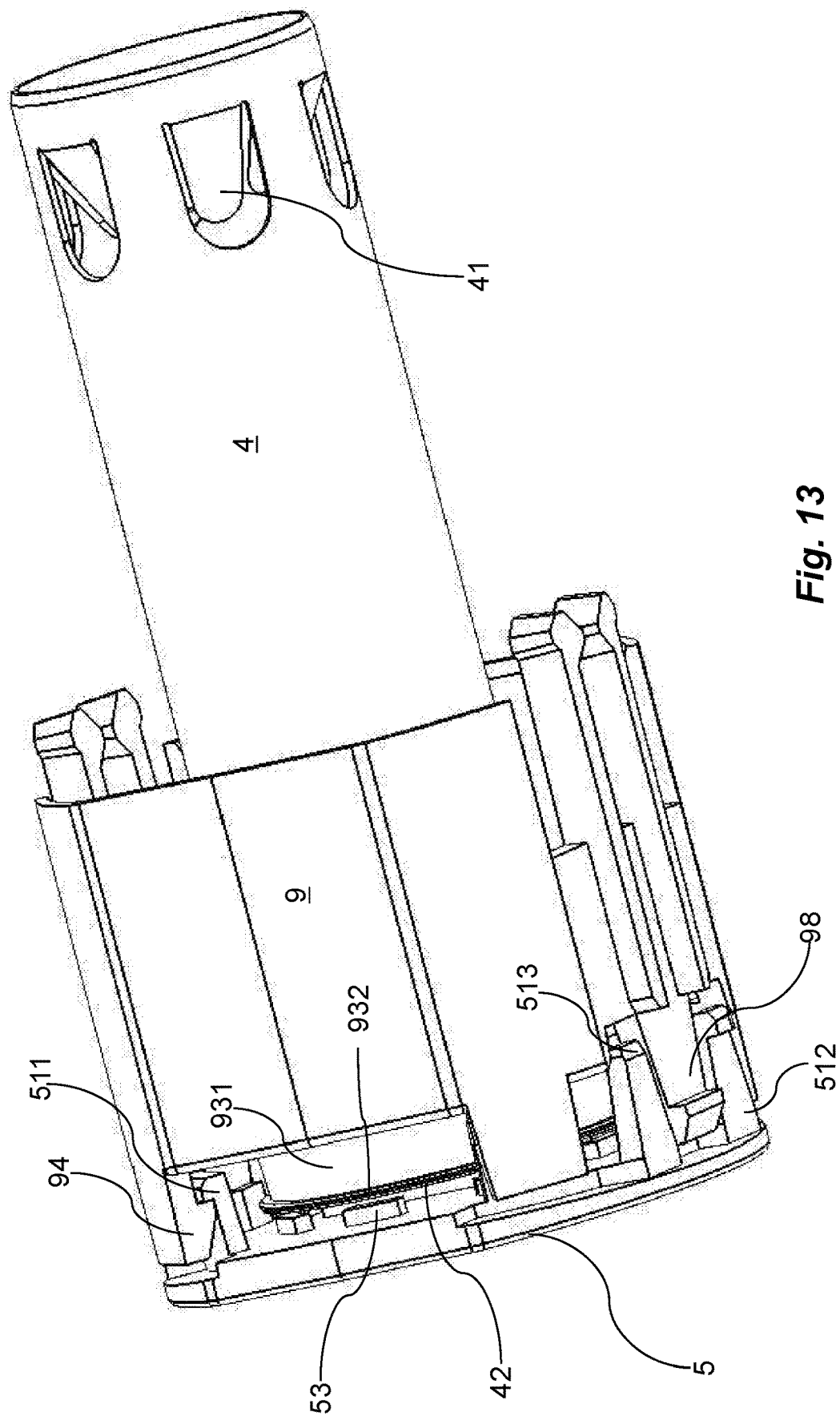
FIG. 13 shows a side view of the cap closer engaged to the inner tubular integrity lock member and the deshielder.

FIG. 13 shows a perspective view of the deshielder 4 assembled proximally to the cap closer 5 and connection between the cap closer 5 and the inner tubular integrity lock member 9. The deshielder 4 is sleeve shaped and having a radially extending outward rim 42 at its proximal end, an opening and inclined engagement elements 41 extending radially inwards and configured to be attached to the RNS/FNS. Further, the wedge shaped engagement elements of the resilient longitudinal proximally extending legs 94 of inner tubular integrity lock member 9 are configured such that they are fixedly engaged with the wedge shaped engagement elements of the distal extending flaps 511 of the cap closer. Thus, the cap closer 5 is fixedly connected to the inner tubular integrity lock member 9. However, it is also possible that the cap closer 5 and the inner tubular integrity lock member 9 are integral. It is also shown that the radially extending outward rim 42 of the deshielder 4 is positioned between the inner circular ledges 53 of the cap closer 5 and the sleeve rim 932 of the integrity lock member 9, such that the deshielder 4 is fixedly attached between the integrity lock member 9 and the cap closer 5.

Figure 14:
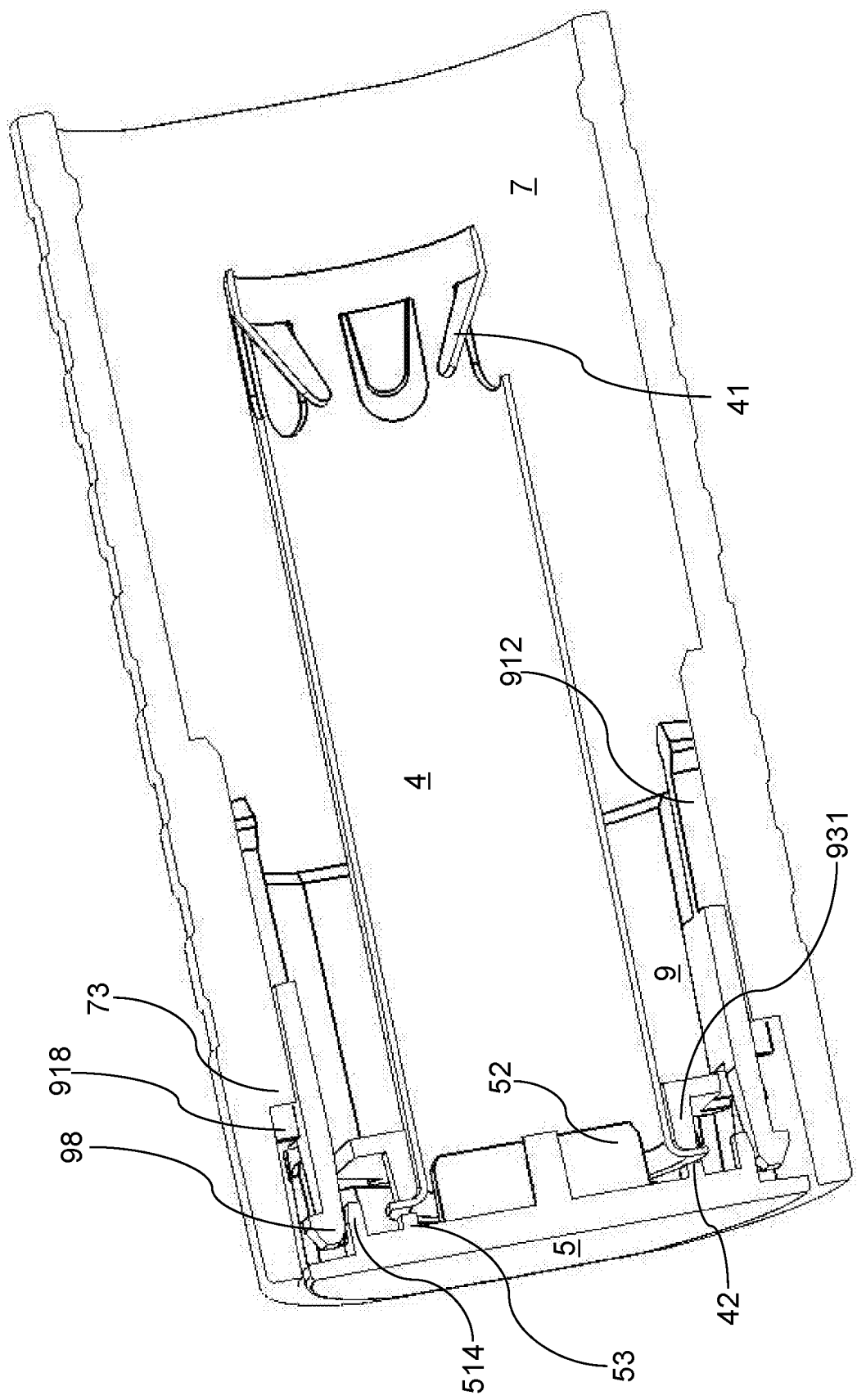
FIG. 14 shows a cross-sectional view of the connections between the cap closer, the integrity lock member, the deshielder and outer tubular cap body when the outer cap body is in the initial position.

FIG. 14 shows a cross-sectional view of the assembled proximal portion of components shown in FIG. 13 having additionally the outer tubular cap body 7 in the initial position. It is shown the H-leg elevation 52 of the cap closer 5 positioned through the opening of the deshielder 4 and the two resilient opposite spaced apart longitudinal proximally extending flaps 98 of the integrity lock member 9 wherein each resilient opposite spaced apart longitudinal proximally extending flap 98 is positioned between one distal extending tongue 512 and one distal extending ledge 513 of the cap closer 5.

The cross-sectional view of FIG. 14 illustrates that the flaps 98 of the integrity lock member 9 abuts radially against the protrusion 514 of the cap closer 5 (not shown in FIG. 14). (not shown in FIG. 10). It can also be seen that the long longitudinal extending rib of the third radial inwardly directed protrusion 73 on the inner surface of the outer tubular cap body 7 is positioned between the radially outward extending ribs 918 for preventing a rotation between the outer tubular cap body 7 in relation to the inner tubular integrity lock member 9 but allowing a longitudinal displacement of the outer tubular cap body 7 in relation to the inner tubular integrity lock member 9.

Figure 15:
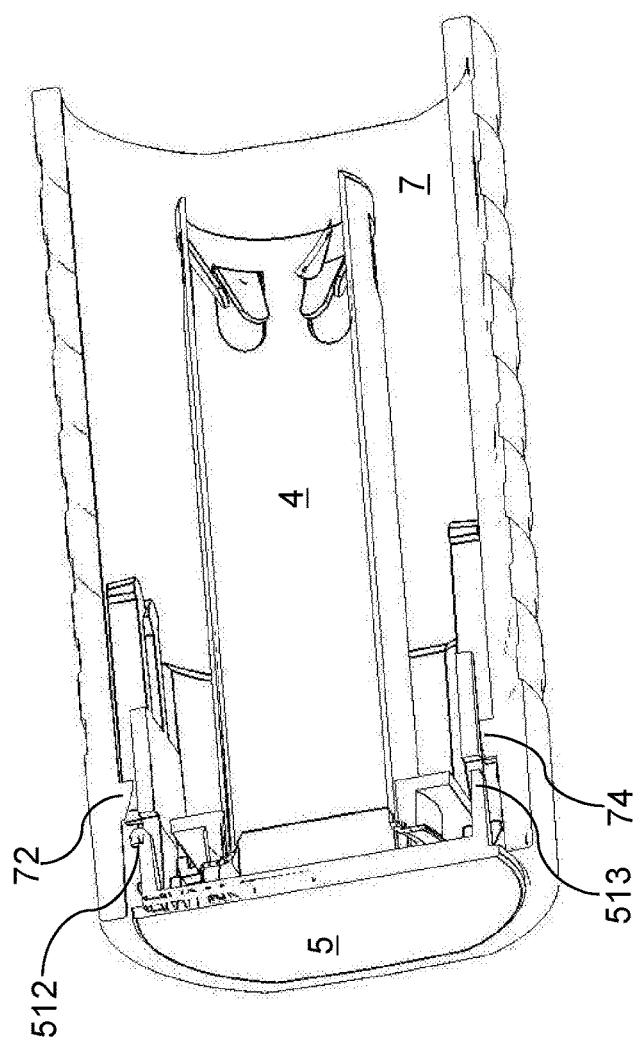
FIG. 15 shows cross-sectional view of FIG. 14 rotated 90 degrees.
Figure 16:
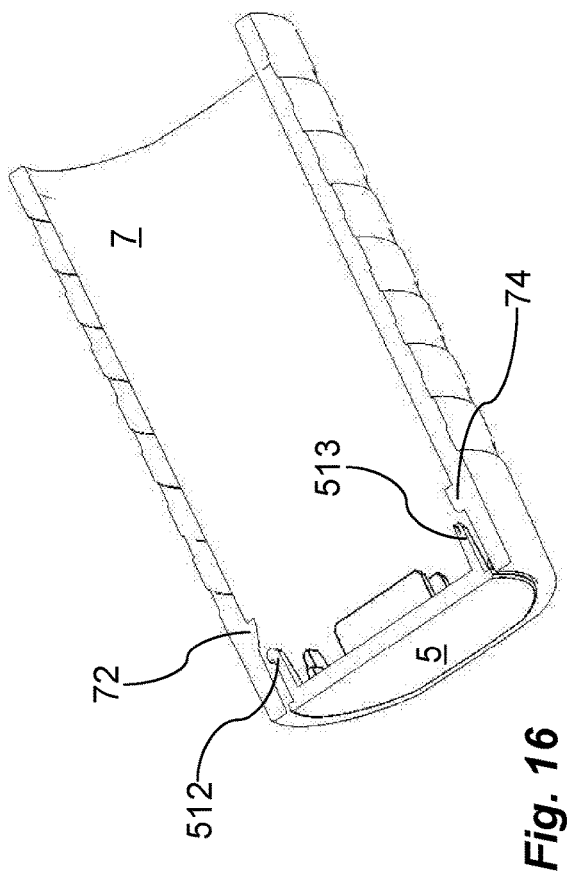
FIG. 16 shows only the cap closer and the outer tubular cap body of FIG. 15.

FIGS. 15-16 show cross-sectional views of FIG. 14 in a different circular angle. It is shown that there is a predetermined distance between one of the first radial inwardly directed protrusions 72 on the inner surface of the outer tubular cap body 7 and the wedge shape engagement of one of the distal extending tongues 512 of the cap closer 5. It is also shown there is a predetermined distance between one of the second radial inwardly directed protrusions 74 on the inner surface of the outer tubular cap body 7 and one of the distal extending ledges 513 of the cap closer 5.

Thus, FIGS. 1, 2 and 13-16 illustrate that the outer tubular cap body 7 is movably arranged in relation to the housing 2 and to the inner tubular integrity lock member 9 from an initial position in which the outer tubular cap body 7 is releasibly connected to the housing 2 and is disengaged from the inner tubular integrity lock member 9.

FIGS. 17-20 illustrate when the outer tubular cap body 7 has been distally pulled by a user from the initial position to an intermediate position in which the outer tubular cap body 7 is partially disengaged from the housing 2 for giving tamper proof indication and in which the outer tubular cap body 7 is fixedly engaged to the inner tubular integrity lock member 9 for allowing the removal of the medicament delivery member shield 6.

Figure 17:
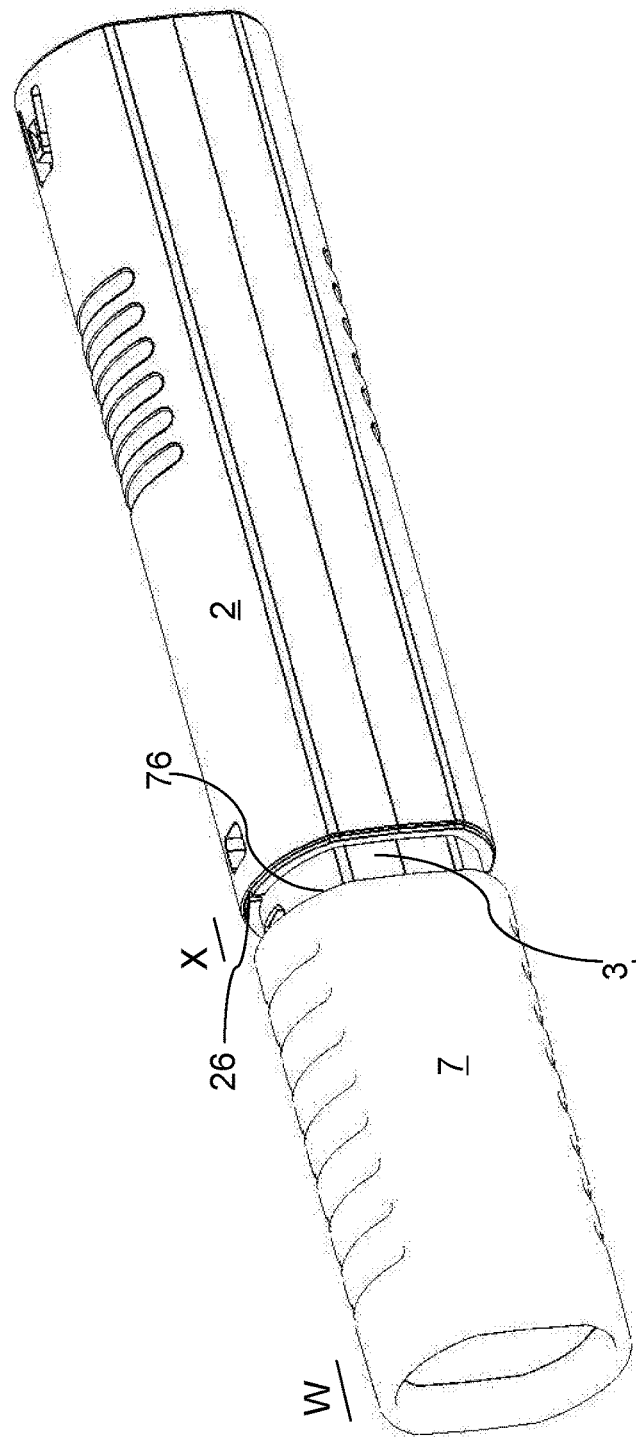
FIG. 17 illustrates the medicament delivery device when the outer tubular cap body is in an intermediate position according to the present invention.
Figure 18:
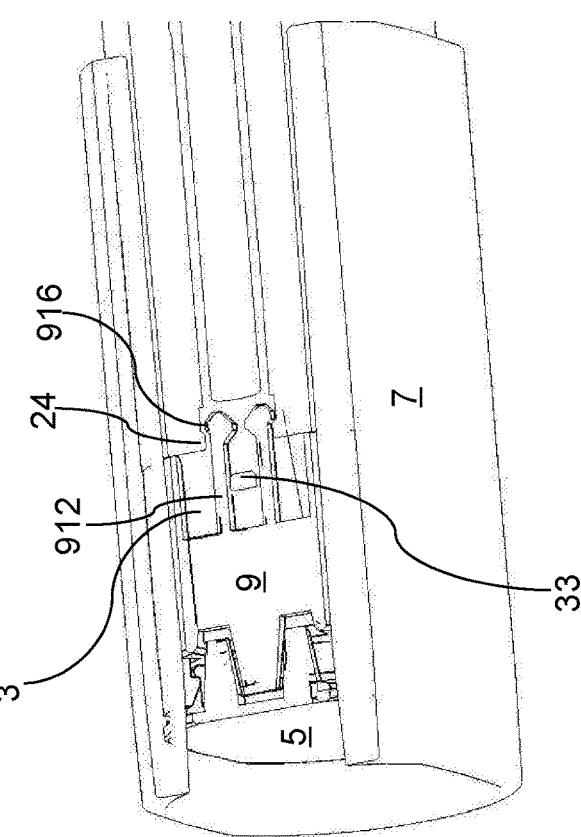
FIG. 18 illustrates transparent view of the outer tubular cap body of FIG. 2, but in the intermediate position.

The "tamper proof indication" can be distinguished when comparing FIG. 1 and 2 (initial position) with FIGS. 17-18 (intermediate position), particularly for the position of the distal rim 76 of the outer tubular cap body 7 in relation to the transversal wall 26 of the housing 2 wherein the transversal wall 26 has been separated longitudinally from the distal rim 76 a predetermined distance X and wherein the outer tubular cap body 7 has been moved in relation to the cap closer 5 a predetermined distance W.

It is important to notice that the resilient structure 91 of the inner tubular integrity lock member 9 is engaged to the first engaging structure 31 and to the second engaging structure 21 in both the initial and intermediate positions of the outer tubular cap body 7 as seen in FIGS. 2 and 12.

Thus, when the outer tubular cap body 7 is in either the initial or in the intermediate position, the resilient structure 91 of the inner tubular integrity lock member 9 is engaged to the first engaging structure 31 of the activation member 3 and to a second engaging structure 21 of the housing 2 in order to prevent the activation member 3 from moving into the retracted position in case that the device 1 is accidentally dropped or activated during transportation. More particularly, the pair of flexible spaced apart longitudinally extending arms 912 extend longitudinally along the bottom wall 35 of the U-shaped guiding recess and receive the guiding protrusion 33, arranged on the bottom wall 35 of the U-shaped guiding recess, in the U-shaped cut-out portion 913 defined by the pair of flexible spaced apart longitudinally extending arms 912.

Further, each second transversal outwardly extending lip 916 is releasably connected to the corresponding side edge 24 of the U-shaped slot or cut-out 20 of the housing 2 for preventing the flexible spaced apart longitudinally extending arms 912 to flex transversally outwards (FIGS. 2 and 18). Moreover, when the outer tubular cap body 7 is in the initial position, the medicament delivery member shield 6, i.e. the RNS/FNS, is attached to medicament container 8, i.e. a syringe and thereby maintaining the sterility of the medicament delivery member 81, i.e. the needle, and the inclined engagement elements 41 of the deshielder 4 are connected to the RNS/FNS.

However, when the outer tubular cap body 6 is moved from the initial to the intermediate position, though the resilient structure 91 of the inner tubular integrity lock member 9 is engaged to the first engaging structure 31 of the activation member 3 and to a second engaging structure 21 of the housing 2 as explained above; there is a risk, due to the components tolerances, that the medicament delivery member shield 6 has moved distally a certain distance in relation to medicament container 8 whereby the sterility of the medicament delivery member 81 has been compromised. Thus, the "tamper proof indication" can be distinguished in the position of the distal rim 76 of the outer tubular cap body 7 in relation to the transversal wall 26 of the housing as seen in FIGS. 17 and 18.

In case that the device 1 is accidentally dropped or activated during transportation i.e. in case that the activation member 3 tries to move into the retracted position, the guiding protrusion 33 arranged on the bottom wall 35 of the guiding recess of the activation member 3 will make contact with first transversal inwardly extending lips 915 and try to force the flexible spaced apart longitudinally extending arms 912 to flex transversally outwards. However, each second transversal outwardly extending lip 916 is releasably connected to the corresponding side edge 24 of the U-shaped slot or cut-out 20 of the housing 2 for preventing the flexible spaced apart longitudinally extending arms 912 to flex transversally outwards and thereby prevent the activation member 3 from moving into the retracted position.

Figure 19:
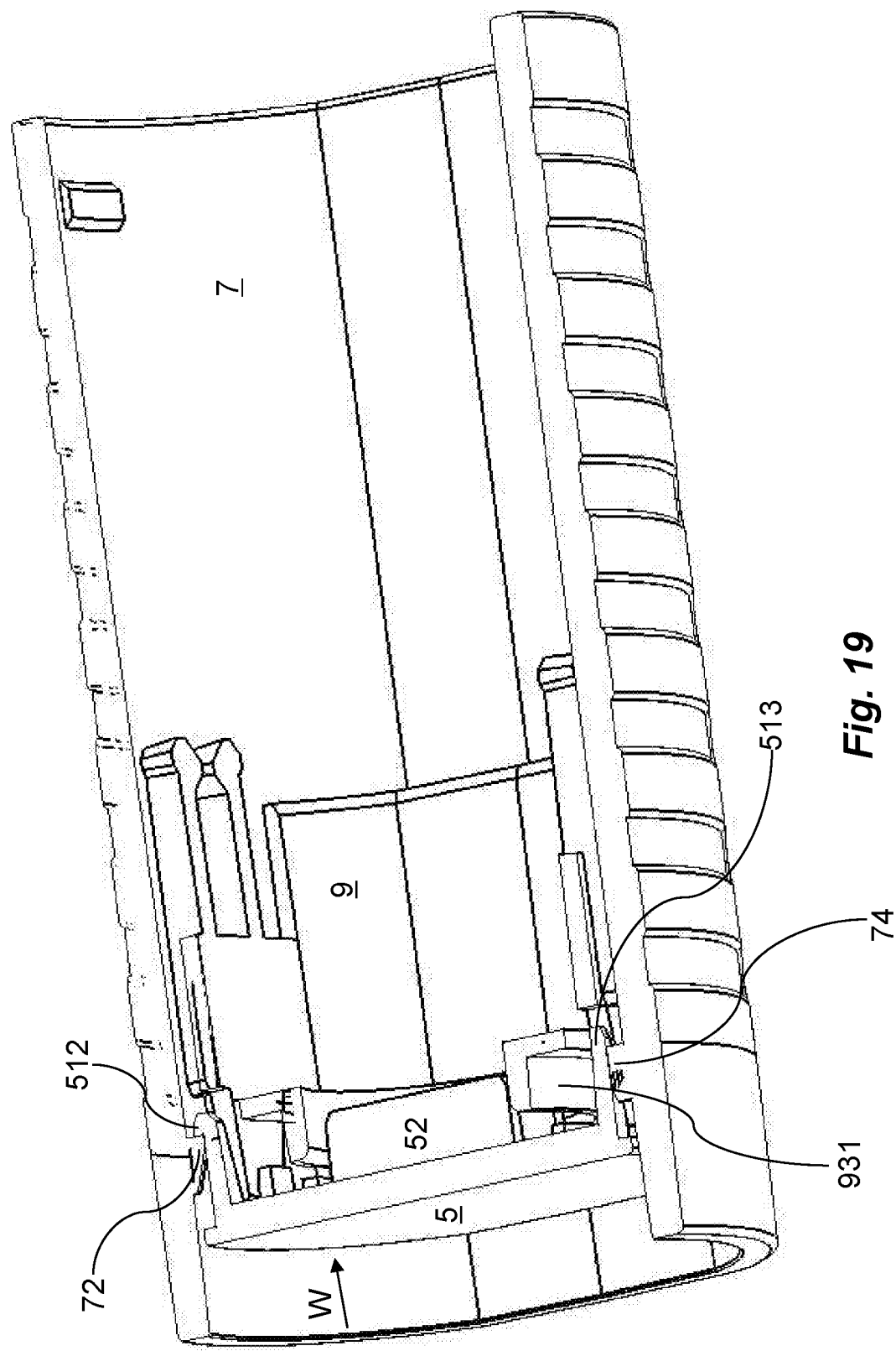
FIG. 19 shows a cross-sectional view of the connections between the cap closer, the integrity lock member, and outer tubular cap body when the outer tubular cap body is in the intermediate position.

FIG. 19 illustrates when the outer tubular cap body 7 is in the intermediate position, more particularly showing when the outer tubular cap body 7 is fixedly engaged to the inner tubular integrity lock member 9 for allowing the removal of the medicament delivery member shield 6.

The outer tubular cap body 7 is fixedly engaged to the inner tubular integrity lock member 9 through the engagement between the first radial inwardly directed protrusions 72 on the inner surface of the outer tubular cap body 7 and the wedge shape engagements of the distal extending tongues 512 of the cap closer 5. It is also depicted that one of the second radial inwardly directed protrusions 74 on the inner surface of the outer tubular cap body 7 and one of the distal extending ledges 513 of the cap closer 5 are radially abutting. Thus the second connecting elements 512, 513 are arranged such that when the outer tubular cap body 7 is in the initial position the first 72, 74 and second 512, 513 connecting elements are disengaged and when the outer tubular cap body 7 is in the intermediate position the first 72, 74 and second connecting elements 512, 513 are engaged.

Figure 20:
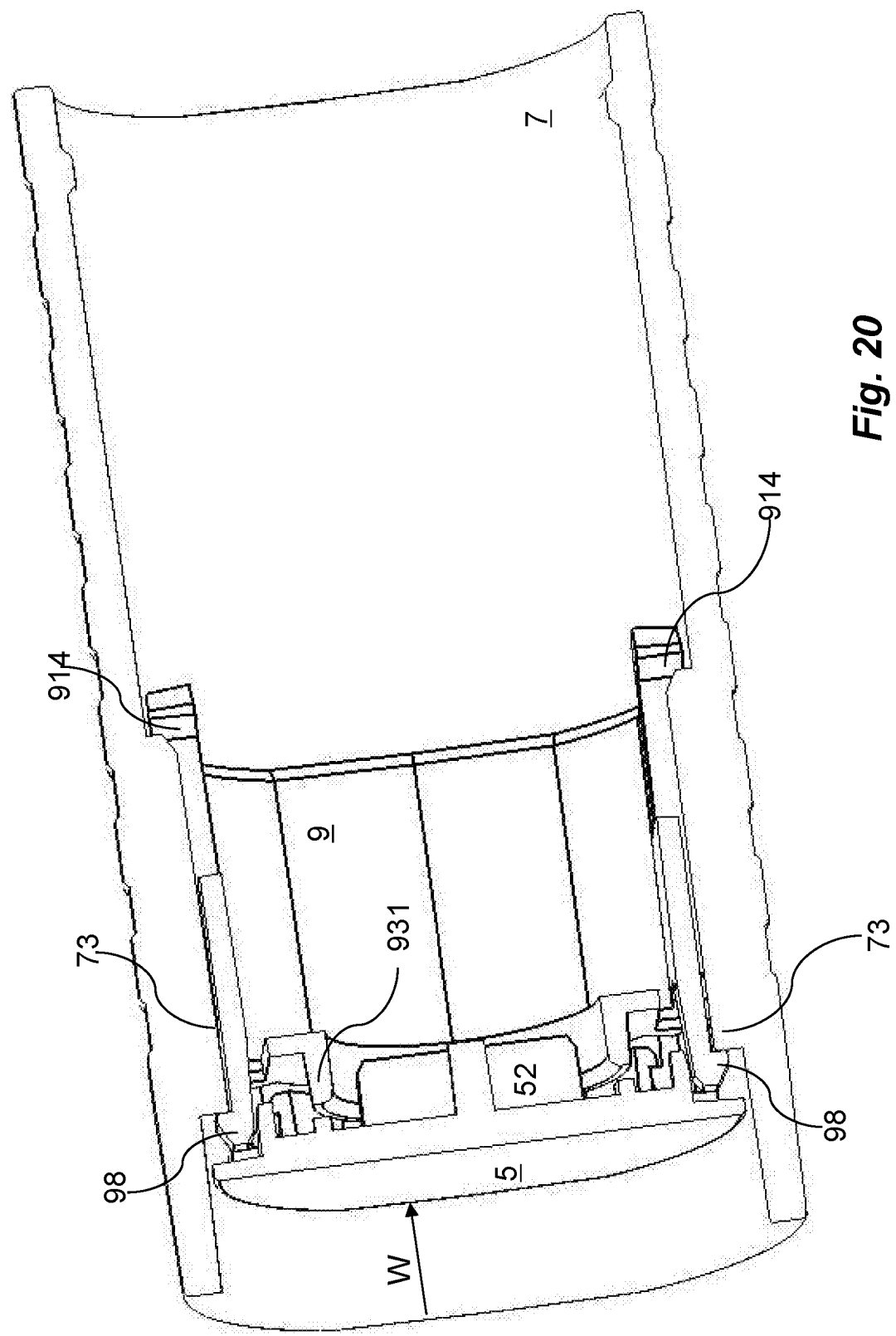
FIG. 20 shows cross-sectional view of FIG. 19 rotated 90 degrees.

FIG. 20 shows a cross-sectional view of FIG. 19 in a different circular angle. The third connecting element 73 and the fourth connecting element 98 are configured to interact when the outer tubular cap body 7 is in the intermediate position such that the outer tubular cap body 7 is fixedly engaged to the inner tubular integrity lock member 9. It is particularly shown how the short circumferential extending rib of the third radial inwardly directed protrusion 73 on the inner surface of the outer tubular cap body 7 abuts against a transversal surface of the wedge shaped engagement element of the resilient opposite spaced apart longitudinal proximally extending flap 98. Due to abutment between the short circumferential extending rib of the third radial inwardly directed protrusion 73 on the inner surface of the outer tubular cap body 7 and the transversal surface of the wedge shaped engagement element of the resilient opposite spaced apart longitudinal proximally extending flap 98, and to the engagement between the first radial inwardly directed protrusions 72 on the inner surface of the outer tubular cap body 7 and the wedge shape engagements of the distal extending tongues 512 of the cap closer 5; the outer tubular cap body 7 is fixedly engaged to the inner tubular integrity lock member 9 resulting in a blocking effect of the outer tubular cap body 7 in relation to the inner tubular integrity lock member 9 on both directions along the L-axis.

Figure 21:
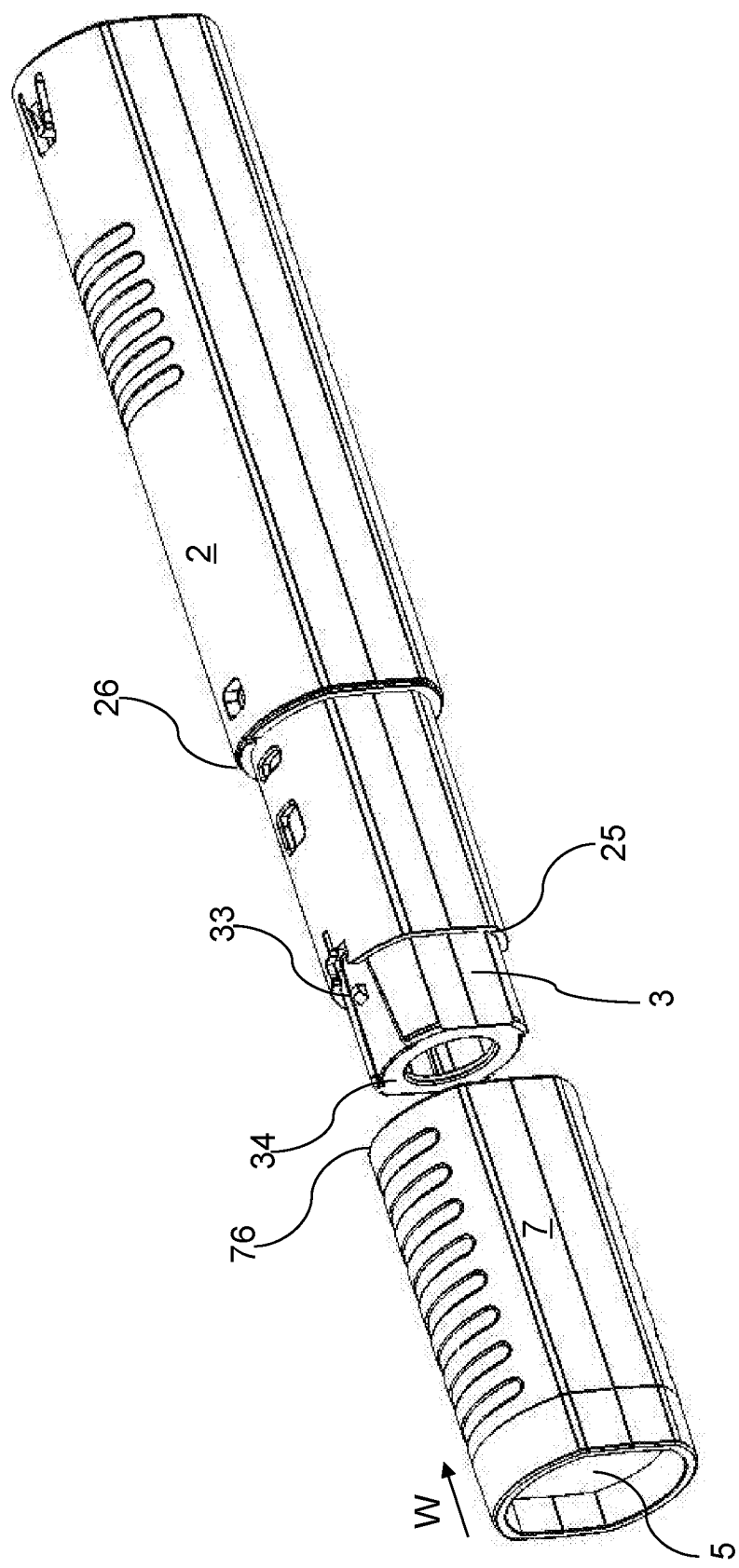
FIG. 21 illustrates the medicament delivery device of the invention in the position of "cap off", when the cap assembly is totally pulled out by the user.

The subsequent and final step after the intermediate position will be described in FIG. 21. According to FIG. 21, the user has manually drawn out the outer tubular cap body 7 along the L-axis from the housing 2 and the activation member 3.

Such movement separates the removable cap assembly to from the tubular housing 2 and from the activation member 3. At the same time the deshielder 4 together with the medicament delivery member shield 6 is separated from the medicament container 8 and exposes the delivery member 81 i.e. the needle which is then surrounded by the activation member 3. The separation of the removable cap assembly to from the tubular housing 2 and from the activation member 3 occurs when the free ends 914 of the flexible spaced apart longitudinally extending arms 912 are disengaged from the first 31 and second 21 engagement structures.

When separated in two parts, the medicament delivery device 1 of the invention cannot be recapped by the user. The cavity formed by the cap closer 5 having the distance W remains visible for the user on the proximally separated portion having: the outer tubular cap body 7, the cap closer 5, the inner integrity lock member 9 and the deshielder 4.

The inventive concept has mainly been described above with reference to the two detailed embodiments. However, as is readily appreciated by a person skilled in the art, other embodiments than the ones disclosed above are equally possible within the scope of the inventive concept, as defined by the appended claims.

The invention claimed is:

1. A medicament delivery device comprising:
   a housing having a proximal end and a distal end, the proximal end the housing comprises a second engaging structure;
   an activation member operably connected to a medicament delivery mechanism and longitudinally movable in relation to the housing from an extended position to a retracted position to active the medicament delivery mechanism, the activation member comprises a first engaging structure; and
   a removable cap assembly comprising an outer tubular cap body, wherein the removable cap assembly further comprises an inner tubular integrity lock member having a resilient structure configured to interact with both the first engaging structure of the activation member and the second engaging structure of the housing so as to prevent the activation member from moving into the retracted position;
   wherein the outer tubular cap body is movable in relation to the housing and to the inner tubular integrity lock member from an initial position in which the outer tubular cap body is releasably connected to the housing and is disengaged from the inner tubular integrity lock member, to an intermediate position, in which the outer tubular cap body is partially disengaged from the housing and in which the outer tubular cap body is fixedly engaged to the inner tubular integrity lock member,
   wherein in the initial or in the intermediate position of the outer tubular cap body, the resilient structure of the inner tubular integrity lock member is configured to interact with both the first and the second engaging structures for preventing the activation member from moving into the retracted position, wherein the first engaging structure of the activation member comprises a guiding recess and a guiding protrusion, and wherein the guiding recess is substantially U-shaped and it is defined by two parallel longitudinally extending side walls, a transversal side wall and a bottom wall and wherein the guiding protrusion is arranged on the outer surface of the bottom wall of the guiding recess.

2. The medicament delivery device according to claim 1, wherein the removable cap assembly further comprises a cap closer which is fixedly or integrally connected to the inner tubular integrity lock member.

3. The medicament delivery device according to claim 2, wherein a deshielder is fixedly attached between the integrity lock member and the cap closer.

4. The medicament delivery device according to claim 3, wherein the outer tubular cap body comprises first connecting elements and the cap closer comprises second connecting elements arranged such that when the outer tubular cap body is in the initial position the first and second connecting elements are disengaged and when the outer tubular cap body is in the intermediate position the first and second connecting elements are engaged.

5. The medicament delivery device according to claim 4, wherein the outer tubular cap body further comprises a third connecting element and the inner tubular integrity lock member a fourth connecting element configured to interact with each other when the outer tubular cap body is in the intermediate position such that the outer tubular cap body is fixedly engaged to the inner tubular integrity lock member.

6. The medicament delivery device according to claim 1, wherein the resilient structure of the inner tubular integrity lock member comprises a pair of spaced apart longitudinally extending arms which are flexible in the transversal direction and which form a U-shaped cut-out portion between them.

7. The medicament delivery device according to claim 6, wherein each longitudinally extending arm has a distal free end having a first transversal inwardly extending lip, a second transversal outwardly extending lip and a distal top edge.

8. The medicament delivery device according to claim 7, wherein the first transversal inwardly extending lip has a shape configured to interact with a corresponding shape of the guiding protrusion for allowing the longitudinally extending arm to flex.

9. The medicament delivery device according to claim 8, wherein in the initial or in the intermediate position of the outer tubular cap body, the pair of spaced apart longitudinally extending arms are configured to extend longitudinally along the bottom wall of the U-shaped guiding recess and to receive the guiding protrusion in U-shaped cut-out portion defined by the pair of spaced apart longitudinally extending arms.

10. The medicament delivery device according to claim 9, wherein the second engaging structure is formed as a U shaped slot or cut-out defined by a transversal edge and two spaced apparat and opposite side edges and wherein each side edge form a transversal inwardly protrusion which presents an edge which forms part of a proximal rim of the housing.

11. The medicament delivery device according to claim 10, wherein each second transversal outwardly extending lip is releasably connected to a corresponding side edge of the U-shaped slot or cut-out of the housing for preventing the longitudinally extending arms to flex transversally outwards and thereby prevent the activation member from moving into the retracted position when the outer tubular cap body is in the initial or in the intermediate position.

12. The medicament delivery device according to claim 1, wherein the medicament delivery device is an auto-injector.

13. A removable cap assembly for a medicament delivery device comprising:
    a housing having a second engagement structure and an activation member having a first engagement structure;
    the removable cap assembly comprising an outer tubular cap body, a cap closer and a deshielder,
    wherein an inner tubular integrity lock member having a resilient structure is configured to interact with both the first engaging structure of the activation member and the second engaging structure of the housing so as to prevent the activation member from moving into the retracted position;
    wherein the removable cap assembly further comprises the outer tubular cap body which is movable in relation to the housing and to the inner tubular integrity lock member from an initial position, to an intermediate position,
    wherein the cap closer is fixedly or integrally connected to the inner tubular integrity lock member, and
    wherein the deshielder is fixedly attached between the integrity lock member and the cap closer.

14. The medicament delivery device according to claim 13, wherein the outer tubular cap body comprises first connecting elements and the cap closer comprises second connecting elements arranged such that when the outer tubular cap body is in the initial position the first and second connecting elements are disengaged and when the outer tubular cap body is in the intermediate position the first and second connecting elements are engaged.

15. The medicament delivery device according to claim 14, wherein the outer tubular cap body further comprises a third connecting element and the inner tubular integrity lock member a fourth connecting element configured to interact with each other when the outer tubular cap body is in the intermediate position such that the outer tubular cap body is fixedly engaged to the inner tubular integrity lock member.

* * * * *